United States Patent [19]

Endo et al.

[11] Patent Number: 5,326,702
[45] Date of Patent: Jul. 5, 1994

[54] BIOLOGICAL PROCESS FOR PRODUCING α-HYDROXYAMIDE OR α-HYDROXY ACID

[75] Inventors: Takakazu Endo, Kanagawa; Tomohide Yamagami, Osaka; Koji Tamura, Kanagawa, all of Japan

[73] Assignee: Nitto Chemical Industry Co., Ltd., Tokyo, Japan

[21] Appl. No.: 791,523
[22] Filed: Nov. 14, 1991
[30] Foreign Application Priority Data Nov. 14, 1990 [JP] Japan .................. 2-308269
[51] Int. Cl.$^5$ .............. C12R 1/01; C12N 1/12; C12P 13/02; C12P 7/42
[52] U.S. Cl. .................. 435/129; 435/130; 435/139; 435/143; 435/145; 435/146; 435/252.1; 435/253.3; 435/822; 435/823; 435/829; 435/830; 435/850; 435/874
[58] Field of Search ............... 435/129, 130, 139, 143, 435/874, 145, 850, 146, 822.3, 829.30, 252.1, 253.3

[56] References Cited

U.S. PATENT DOCUMENTS

| D. 931,391 | 6/1990 | Enomoto et al. ............ 435/188 |
| 5,2000,331 | 4/1993 | Kawakami et al. ........... 435/129 |
| 4,001,081 | 1/1977 | Commeyras et al. .......... 435/832 |
| 4,800,162 | 1/1989 | Matson ........................ 435/280 |
| 4,900,672 | 2/1990 | Yamada et al. ............... 435/188 |
| 4,908,313 | 3/1990 | Satoh et al. .................. 435/129 |
| 5,089,405 | 2/1992 | Cerelaud et al. ............. 435/141 |
| 5,130,235 | 7/1992 | Beppu et al. ................. 435/129 |
| 5,179,014 | 1/1993 | Watanabe et al. ............ 435/125 |

FOREIGN PATENT DOCUMENTS

| 204555 | of 0000 | European Pat. Off. ....... 435/129 |
| 188252 | 7/1986 | European Pat. Off. ....... 435/129 |
| 307926 | 3/1989 | European Pat. Off. ....... 435/129 |
| 034901 | 3/1990 | European Pat. Off. . |
| 2245585 | 4/1975 | France . |
| 2294999 | 7/1976 | France . |
| 5275 | 4/1992 | World Int. Prop. O. ...... 435/129 |

OTHER PUBLICATIONS

Chemical Abstracts, vol., 105, No. 7, Aug. 18, 1986, Columbus, Ohio, U.S., Abstract No. 59481x Kawakami et al., "Microbial Production of Alpha Hydroxy Acid and its Salts", p. 518.
Ogata, Y. and Kawasaki, A., "Equilibrium Additions to Carbonyl Compounds", (1970) *The Chemistry of the Carbonyl Group*, vol. 2, pp. 1-36.

Primary Examiner—Herbert J. Lilling
Attorney, Agent, or Firm—Sughrue, Mion, Zinn, Macpeak & Seas

[57] ABSTRACT

A process for biologically producing an α-hydroxyamide or an α-hydroxy acid represented by formula (III)

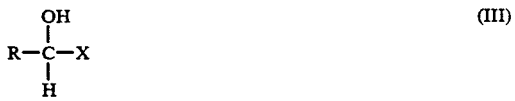

wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group or a substituted or unsubstituted and saturated or unsaturated heterocyclic group; and X represents an amido group or a carboxyl group, comprising reacting an α-hydroxynitrile represented by formula (I):

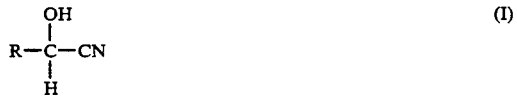

wherein R is as defined above, or a mixture of an aldehyde represented by formula (II):

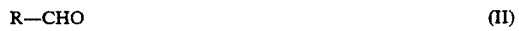

wherein R is as defined above, and hydrogen cyanide with a microorganism capable of producing such an amide or acid from the corresponding α-hydroxynitrile is disclosed, in which the reaction system contains a sulfite ion, a disulfite ion or a dithionite ion. The enzymatic activity of the microorganism lasts for an extended period of time.

9 Claims, No Drawings

BIOLOGICAL PROCESS FOR PRODUCING α-HYDROXYAMIDE OR α-HYDROXY ACID

FIELD OF THE INVENTION

The invention relates to a biological process for producing an α-hydroxyamide or an α-hydroxy acid.

BACKGROUND OF THE INVENTION

Known biological processes for producing an α-hydroxyamide include a process comprising reacting lactonitrile, hydroxyacetonitrile, α-hydroxymethylthiobutyronitrile etc. with a microorganism belonging to the genus Bacillus, Bacteridium, Micrococcus or Brevibacterium to obtain a corresponding amide as disclosed in JP-B-62-21519 (corresponding to U.S. Pat. No. 4,001,081) (the term "JP-B" as used herein means an "examined published Japanese patent application"). It is also reported in Grant, D. J. W., *Antonie van Leeuwenhoek; J. Microbiol. Serol.* Vol. 39, p. 273 (1973) that hydrolysis of lactonitrile by the action of a microorganism belonging to the genus Corynebacterium to produce lactic acid involves accumulation of lactamide as an intermediate.

Known biological processes for producing an α-hydroxy acid include a process for obtaining glycolic acid, lactic acid, α-hydroxyisobutyric acid etc. from the corresponding α-hydroxynitrile by the action of a microorganism of the genus *Corynebacterium (see JP-A-61-56086*, the term "JP-A" as used herein means an "unexamined published Japanese patent application"), a process for obtaining lactic acid, glycolic acid etc. from the corresponding α-hydroxynitrile by using a microorganism of the genus Bacillus, Bacteridium, Micrococcus or Brevibacterium (see JP-B-58-15120, corresponding to U.S. Pat. No. 3,940,316), a process for obtaining lactic acid, α-hydroxyisobutyric acid, mandelic acid, α-hydroxybutyric acid, α-hydroxyvaleric acid, α-hydroxy-α-phenylpropionic acid, α-hydroxy-α-(p-isobutylphenyl)propionic acid etc. from the corresponding α-hydroxynitrile by using a microorganism of the genus Pseudomonas, Arthrobacter, Aspergillus, Penicillium, Cochliobolus or Fusarium (see JP-A-63-222696) and a process for obtaining α-hydroxy-β,β-dimethyl-γ-butyrolactone from the corresponding α-hydroxynitrile by using a microorganism of the genus Arthrobacter. Aspergillus, Bacillus, Bacteridium, Brevibacterium, Cochliobolus, Corynebacterium. Micrococcus, Nocardia. Penicillium, Pseudomonas or Fusarium (see JP-A-64-10996).

It is known, however, that an α-hydroxynitrile is, more or less, partially dissociated into the corresponding aldehyde and hydrogen cyanide in a polar solvent as taught in V. Okano et al., *J. Am. Chem. Soc.*, Vol. 98, p. 4201 (1976). Since an aldehyde generally is bound to proteins to deactivate enzymes as described in G. E. Means et al. (ed.), *Chemical Modification of Proteins*, p. 125, Holden-Day (1971), enzymatic hydration or hydrolysis of an α-hydroxynitrile is accompanied with the problem that the enzyme is deactivated in a short time. It therefore has been difficult to obtain an α-hydroxyamide or an α-hydroxy acid in high concentration with high productivity.

SUMMARY OF THE INVENTION

To overcome the above-described problem associated with conventional biological processes for producing an α-hydroxyamide or an α-hydroxy acid, the inventors conducted extensive investigations and, as a result, found that the presence of a sulfite ion, a disulfite ion or a dithionite ion in the reaction system markedly improves activity and stability of enzymes and solved the above-described problem.

The present invention provides a biological process for producing an α-hydroxyamide or an α-hydroxy acid represented by formula (III):

wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group or a substituted or unsubstituted and saturated or unsaturated heterocyclic group; and X represents an amido group or a carboxyl group, comprising reacting an α-hydroxynitrile represented by formula (I):

wherein R is as defined above, or a mixture of an aldehyde represented by formula (II):

wherein R is as defined above, and hydrogen cyanide with a microorganism capable of producing such an amide or acid from the corresponding α-hydroxynitrile, in which the reaction system contains a sulfite ion, a disulfite ion or a dithionite ion.

DETAILED DESCRIPTION OF THE INVENTION

A sulfite ion, a disulfite ion or a dithionite ion added to the reaction system is supplied as, for example, sodium sulfite, sodium bisulfite, sodium dithionite, potassium sulfite, potassium bisulfite, potassium dithionite, ammonium sulfite, ammonium bisulfite or ammonium dithionite.

The following mechanism is suggested to account for the action of those ions. A sulfite ion, a disulfite ion or a dithionite ion has properties of forming a complex with an aldehyde. That is, those ions rapidly react with an aldehyde released by dissociation of an α-hydroxynitrile in a polar solvent to form a complex, thus serving to maintain a low free aldehyde concentration in the reaction system. The complex formed undergoes a nucleophilic reaction with a proton or hydrogen cyanide to release reversibly an aldehyde or an α-hydroxynitrile, respectively.

According to the present invention, hydration or hydrolysis of a nitrile can be carried on while maintaining a low aldehyde concentration in the reaction system by a combination of those actions so that the enzyme inhibitory action of the aldehyde is minimized and the reaction can last for an extended period of time, in a stable manner, without causing drastic deactivation of the enzyme making it possible to accumulate the produced amide or acid in high concentrations. It is still obscure, however, whether the enzyme stabilization mechanism by a sulfite ion, a disulfite ion or a dithionite ion is attributable only to the reduction in free aldehyde concentration in the reaction system.

Considering the above-stated fact that an aldehyde generally has properties of binding to proteins to deactivate an enzyme, it appears that the inhibitory effect on enzyme activity by a sulfite ion, a disulfite ion or a dithionite ion applies to all biological reactions which involve an aldehyde. In other words, the microorganism which can be used in the production of an amide or an acid from an α-hydroxynitrile according to the present invention is not particularly limited as long as the microorganism is capable of producing such an amide or acid from the corresponding α-hydroxynitrile. Likewise, the α-hydroxynitrile substrate is not particularly limited as long as it reaches a dissociation equilibrium with an aldehyde in the reaction system.

Microorganisms capable of hydrolyzing an α-hydroxynitrile to convert it to the corresponding acid include those belonging to the genus Pseudomonas, Alcaligenes, Acinetobacter, Caseobacter, Corynebacterium, Brevibacterium, Nocardia, Rhodococcus, Arthrobacter, Bacillus, Aureobacterium, Enterobacter, Escherichia, Micrococcus, Strectomyces, Flavobacterium, Aeromonas, Mycoplana, Cellulomonas, Erwinia, Candida, Bacteridium, Aspergillus, Penicillium, Cochliobolus, Fusarium or Rhodopseudomonas.

Specific species of those microorganisms are Pseudomonas sp. BC13-2 (FERM BP-3319), Pseudomonas sp. BC15-2 (FERM BP-3320), Pseudomonas sp. SK13 (FERM BP-3325), Pseudomonas sp. SK31 (FERM P-11310), Pseudomonas sp. SK87 (FERM P-11311), *Pseudomonas synxanta* IAM 12356, Alcaligenes sp. BC12-2 (FERM P-11263), Alcaligenes sp. BC20 (FERM P-11264), Alcaligenes sp. BC35-2 (FERM BP-3318), Acinetobacter sp. BC9-2 (FERM BP-3317), Caseobacter sp BC4 (FERM BP-3316), Caseobacter BC23 (FERM P-11261), *Corynebacterium nitrilophilus* ATCC 21419, *Brevibacterium acetylicum* IAM 1790, *Brevibacterium helvolum* ATCC 11822, Nocardia sp. N-775 (FERM BP-961), *Nocardia asteroides* IFO 3384, *Nocardia calcarea* KCC A0191, *Nocardia polychromogenes* IFM 19, Rhodococcus sp. SK70 (FERM P-11304), Rhodococcus sp. SK92 (FERM BP-3324), Rhodococcus sp. HR11 (FERM P-11306), *Rhodococcus rhodochrous* ATCC 12674, *Rhodococcus rhodochrous* ATCC 19140, *Rhodococcus rhodochrous* ATCC 33258, *Rhodococcus erythropolis* IFM 155, IFO 12320, IFO 12538 and IFO 12540, Arthrobacter sp. SK103 (FERM P-11300), Arthrobacter sp. HR1 (FERM BP-3323), Arthrobacter sp. HR4 (FERM P-11302), *Arthrobacter oxydans* IFO 12138, *Bacillus subtilis* ATCC 21697, *Bacillus licheniformis* IFO 12197, *Bacillus megaterium* ATCC 25833, *Aureobacterium testaceum* IAM 1561, Enterobacter sp. SK12 (FERM BP-3322), *Escherichia coli* IFO 3301, *Micrococcus luteus* ATCC 383, *Micrococcus varians* IAM 1099, *Micrococcus roseus* IFO 3768, *Streptomyces griseus* IFO 3355, Flavobacterium sp. SK150 (FERM P-11645), *Flavobacterium flavescens* ATCC 8315, *Aeromonas punctata* IFO 13288, *Mycoplana dimorpha* ATCC 4297, *Cellulomonas fimi* IAM 12107, *Erwinia herbicola* IFO 12686 and *Candida quilliermondii* IFO 0566. The details of the above-enumerated microorganisms are set forth in Japanese Patent Application Nos. Hei-2-80694, Hei-2-148723, Hei-2-148725, Hei-2-214914, Hei-2-214915 and Hei-2-214916, and U.S. Ser. Nos. 07/677,175 (filed on Mar. 29, 1991) and 07/745,297 (filed on Aug. 15, 1991)

In addition, the microorganisms disclosed in JP-B-58-15120 (corresponding to U.S. Pat. No. 3,940,316, JP-A-61-56086, JP-A-63-222696, JP-A-64-10996), and JP-A-2-84198 (corresponding to EPO 0 348 901A2) also are suitable.

Microorganisms capable of hydrating an α-hydroxynitrile to convert it to the corresponding amide include those belonging to the genus Rhodococcus, Corynebacterium, Pseudomonas, Arthrobacter, Alcaligenes, Bacillus, Bacteridium, Micrococcus, Brevibacterium or Nocardia.

Specific species of those microorganisms are *Rhodococcus rhodochrous* ATCC 33278, *Rhodococcus erythropolis* IFO 12320, *Corynebacterium nitrilophilus* ATCC 21419, Pseudomonas sp. SK87 (FERM P-11311), Arthrobacter sp. HR1 (FERM BP-3323) and Alcaligenes sp. BC16-2 (FERM BP-3321). The details of those microorganisms are set forth in Japanese Patent Application No. Hei-2-148724. In addition, the microorganisms disclosed in JP-B-62-21519 (corresponding to U.S. Pat. No. 4,001,081) also are suitable.

Of the above-mentioned strains, Pseudomonas sp. BC13-2, BC15-2, SK13, SK31 and SK87, Alcaligenes sp. BC 12-2, BC20, BC35-2 and BC16-2; Acinetobacter sp. BC9-2; Caseobacter sp. BC4 and BC23; Rhodococcus sp. SK70, SK92 and HR11 ; Arthrobacter sp. SK103, HR1 and HR4; Enterobacter sp. SK12; and Flavobacterium sp. SK150 are new strains isolated by the inventors from the soil and have been deposited with Fermentation Research Institute, Agency of Industrial Science & Technology, Tsukuba, Japan under the respective deposit numbers (FERM Nos.). Morphologic and physiologic properties of those new strains are described below. All the other microorganisms are known and are available from American Type Culture Collection, Rockville, Md. USA (ATCC), Institute of Applied Microbiology, The University of Tokyo, Tokyo, Japan (IAM), Fermentation Research Institute, Agency of Industrial Science & Technology, Tsukuba, Japan (FRI), Kaken Pharmaceutical Company, Ltd., Tokyo, Japan (KCC), Institute for Fermentation, Osaka, Japan (IFO) or Research Institute for Chemobiodynamics, The University of Chiba, Chiba, Japan (IFM) under the above-enumerated respective deposit numbers.

| Taxonomic Properties: | |
|---|---|
| BC13-2 and BC15-2 Strains: | |
| Shape: | bacillus |
| Gram's stain: | − |
| Spore: | − |
| Mobility: | + |
| Flagellum: | polar |
| Oxidase: | + |
| Catalase: | + |
| O-F test: | O |
| SK13, SK31, and SK87 Strains: | |
| Shape: | bacillus |
| Grams's stain: | − |
| Spore: | − |
| Mobility: | + |
| Flagellum: | polar |
| Oxidase: | + |
| Catalase: | + |
| O-F test: | O |
| BC12-2 and BC20 Strains: | |
| Shape: | bacillus |

| Taxonomic Properties: | |
|---|---|
| Gram's stain: | − |
| Spore: | − |
| Mobility: | + |
| Flagellum: | peripheral |
| Oxidase: | + |
| Catalase: | + |
| O-F test: | alkalization |
| 3-Ketolactose production: | − |
| Existence of quinone: | Q-8 |
| BC35-2 and BC16-2 Strains: | |
| Shape: | bacillus |
| Gram's stain: | − |
| Spore: | − |
| Mobility: | + |
| Flagellum: | peripheral |
| Oxidase: | + |
| Catalase: | + |
| O-F test: | alkalization |
| 3-Ketolactose production: | − |
| Existence of quinone: | Q-8 |
| BC9-2 Strain: | |
| Shape: | bacillus |
| Grams's stain: | − |
| Spore: | − |
| Mobility: | − |
| Oxidase: | − |
| Catalase: | + |
| O-F test: | − |
| BC4 and BC23 Strains: | |
| Shape: | polymorphic bacillus |
| Gram's stain: | + |
| Spore: | − |
| Mobility: | − |
| Oxidase: | − |
| Catalase: | + |
| Rod-coccus cycle: | + |
| Extension of periphery of colony: | not observed |
| Growth under anaerobic condition: | − |
| Diamino acid of cell wall: | meso-diaminopimelic acid |
| Glycolyl test: | − (acetyl type) |
| Sugar composition of cell wall: | |
| Arabinose: | + |
| Galactose: | + |
| Existence of quinone: | MK-8 (H$_2$) |
| SK70, SK92, and HR11 Strains: | |
| Shape: | polymorphic bacillus |
| Gram's stain: | + |
| Spore: | − |
| Mobility: | − |
| Oxidase: | − |
| Catalase: | + |
| Rod-coccus cycle: | − |
| Extension of periphery of colony: | not observed |
| Growth under anaerobic condition: | − |
| Diamino acid of cell wall: | meso-diaminopimelic acid |
| Glycolyl test: | + (glycolyl type) |
| Sugar composition of cell wall: | |
| Arabinose: | + |
| Galactose: | + |
| Existence of quinone: | MK-8 (H$_2$) |
| SK103, HR1, and HR4 Strains: | |
| Shape: | polymorphic bacillus |
| Gram's stain: | + |
| Spore: | − |
| Mobility: | − |
| Oxidase: | − |
| Catalase: | + |
| Rod-coccus cycle: | + |
| Extension of periphery of colony: | not observed |
| Growth under anaerobic condition: | − |
| Diamino acid of cell wall: | lysine |
| Glycolyl test: | − (acetyl type) |
| Sugar composition of cell wall: | |

| Taxonomic Properties: | |
|---|---|
| Arabinose: | − |
| Galactose: | − |
| Existence of quinone: | MK-9 (H$_2$) |
| SK12 Strain: | |
| Shape: | bacillus |
| Gram's stain: | − |
| Spore: | − |
| Mobility: | + |
| Oxidase: | − |
| Catalase: | + |
| O-F test: | F |
| Production of gas from glucose: | − |
| Indole production: | − |
| Methyl Red: | + |
| V-P: | − |
| Utilization of citric acid: | + |
| Production of hydrogen sulfide: | − |
| Decomposition of urea: | − |
| Deamination reaction of phenylalanine: | + |
| Decarboxylation reaction of lysine: | − |
| Arginine dihydrolase: | − |
| Decarboxylation reaction of ornithine: | − |
| SK150 Strain: | |
| Shape: | bacillus |
| Grams' stain: | − |
| Spore: | − |
| Mobility: | − |
| Flagellum: | − |
| Oxidase: | + |
| Catalase: | + |
| O-F test: | O |
| Production of pigment: | water-insoluble yellow pigment |

Abbreviation
O-F test: Oxidation-Fermentation test
V-P test: Voges-Proskauer test
MK: Menaquinone
Q: Quinone The α-hydroxynitrile which can be used as a substrate in the present invention is represented by formula (I), wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group or a substituted or unsubstituted and saturated or unsaturated heterocyclic group. The α-hydroxynitrile of formula (I) releases an aldehyde and hydrogen cyanide in polar solvents such as water and buffers and the thus released aldehyde forms a complex with a sulfite ion, a disulfite ion or a dithionite ion.

In formula (I), the heterocyclic group includes those containing at least one of a nitrogen atom, an oxygen atom, and a sulfur atom as a hetero atom. Substituents of the heterocyclic group include an alkyl group, an alkoxy group, an acyl group, an aryl group, an aryloxy group, a halogen atom, e.g., chlorine and bromine, a hydroxyl group, an amino group, a nitro group and a thiol group.

Specific examples of α-hydroxynitriles of formula (I) are lactonitrile, α-hydroxy-n-propionitrile, α-hydroxy-n-butyronitrile, α-hydroxyisobutyronitrile, α-hydroxy-n-hexylonitrile, α-hydroxy-n-heptylonitrile, α-hydroxy-noctylonitrile, α,γ-dihydroxy-β,β-dimethylbutyronitrile, acrolein cyanhydrin, methacrylaldehyde cyanhydrin, 3-chlorolactonitrile, 4-methylthio-α-hydroxybutyronitrile, α-hydroxy-α-phenylpropionitrile and substituted compounds thereof. Examples of α-hydroxynitriles of formula (I) having an aromatic or heterocyclic group are mandelonitrile, 2-thiophenecarboxyaldehyde cyanhydrin, 2-pyridinecarboxyaldehyde cyanhydrin, 2-pyrrolecarboxyaldehyde cyanhydrin, 2-furaldehyde cyanhydrin, 2-naphthylaldehyde cyanhydrin and substituted compounds thereof.

When a microorganism having a stereospecific nitrile hydratase or hydrolase is used in the biological reaction, the whole product, an α-hydroxyamide or an α-hydroxy acid, can be converted easily to either one of the optically active compounds. In the present invention, therefore, an α-hydroxyamide or an α-hydroxy acid can be obtained stereospecifically with extreme advantage over the conventional processes involving optical resolution and/or racemization.

The hydration or hydrolysis reaction of an α-hydroxynitrile of formula (I) can be effected by contacting the α-hydroxynitrile or a mixture of an aldehyde of formula (II) and hydrogen cyanide with microbial cells or treated microbial cells (e.g., ruptured microbial cells, a crude or purified enzyme, immobilized microbial cells or immobilized enzyme) of a microorganism in an aqueous medium, such as water and a buffer. A sulfite ion, a disulfite ion or a dithionite ion is added to the reaction system usually in a concentration of from about 1 mM to about 1000 mM.

The substrate concentration in the reaction system usually ranges from 0.1 to 10% by weight, and preferably from 0.2 to 5.0% by weight, on concentration to an α-hydroxynitrile. The concentrations of aldehyde and hydrogen cyanide in the reaction system usually range from 0.1 to 10% by weight, preferably 0.2 to 5.0% by weight and 0.1 to 1.0% by weight, preferably from 0.1 to 0.5% by weight, respectively. A microorganism is used in an amount of from 0.01 to 5.0% by weight on a dry basis based on the substrate. The reaction is usually performed at a temperature of from the freezing point to 50° C., and preferably from 10° to 30° C., for a period of from 0.1 to 100 hours.

Where the α-hydroxynitrile has considerably low solubility in the aqueous medium used, it is recommended for achieving efficient reaction to add from 0.1 to 5.0% by weight of an appropriate surface active agent, e.g., Triton X-100 (polyethylene glycol p-isooctylphenyl ether) and Tween 60 (polyoxyethylene sorbitan monostearate), or an auxiliary solvent, e.g., methanol, ethanol and dimethyl sulfoxide, to the reaction system.

Thus, the α-hydroxynitrile is converted to the corresponding amide or acid by the hydrating or hydrolytic activity of the microorganism and the product accumulates in the reaction system. After removing microbial cells and any other insoluble matter from the reaction system, the product can be isolated by known means, such as concentration, ion-exchange, electrical dialysis, extraction and crystallization.

The present invention is now illustrated in greater detail with reference to Examples, but it should be understood that the present invention is not deemed to be limited thereto. All the percents are by weight unless otherwise indicated.

EXAMPLE 1

Alcaligenes sp. BC35-2 (FERM No. 11265; FERM BP-3318) was suspended in 0.8 ml of a 50 mM phosphoric acid buffer (pH=7.5) containing 14 mM of mandelonitrile and a prescribed amount, as noted in Table 1 below, of sodium sulfite to prepare a cell suspension having an optical density at 630 nm ($OD_{630}$) of 9. The cell suspension was incubated at 30° C. for 4 minutes followed by centrifugation to remove the microbial cells. For comparison, the same reaction was conducted except for using a substrate solution containing no sodium sulfite.

The separated supernatant was analyzed by liquid chromatography using a column "SHODEX ODS F511A produced by Showadenko K.K., Japan" to determine mandelic acid produced. Further, the optical purity of the mandelic acid was measured by using a column "CHIRALPAC WH produced by Daicel Chemical Industries, Ltd., Japan". The results obtained are shown in Table 1.

TABLE 1

| $Na_2SO_3$ Concentration (mM) | Mandelic Acid Produced (mM) | Optical Purity of R(−) Compound (%age) |
|---|---|---|
| 0 | 4.8 | 98 |
| 20 | 7.5 | 98 |
| 50 | 8.0 | 98 |
| 100 | 8.4 | 98 |
| 200 | 6.2 | 98 |
| 600 | 5.5 | 97 |
| 1000 | 4.0 | 98 |

EXAMPLE 2

The same procedures as in Example 1 were followed, except for replacing sodium sulfite by sodium disulfite. The results obtained are shown in Table 2 below.

TABLE 2

| $NaHSO_3$ Concentration (mM) | Mandelic Acid Produced (mM) | Optical Purity of R(−) Compound (%age) |
|---|---|---|
| 0 | 4.4 | 98 |
| 20 | 8.1 | 97 |
| 100 | 9.8 | 98 |
| 200 | 6.9 | 97 |
| 600 | 5.1 | 98 |
| 1000 | 4.1 | 98 |

EXAMPLE 3

Each of strains of Alcaligenes sp. BC35-2 (FERM No. 11265; FERM BP-3318), Pseudomonas sp. BC13-2 (FERM No. 11266; FERM BP-3316), Caseobacter sp. BC4 (FERM No. 11260; FERM BP-3316), Acinetobacter sp. BC9-2 (FERM No. 11262; FERM BP-3317), Nocardia asteroides IFO 3384, Bacillus subtilis ATCC 21697, Brevibacterium acetylicum IAM 1790, Aureobacterium testaceum IAM 1561 and Alcaligenes fecalis ATCC 8750 was suspended in 0.8 ml of a 50 mM phosphoric acid buffer (pH=7.5) containing 14 mM mandelonitrile or its derivative, shown in Table 3 below, and 100 mM sodium sulfite to prepare a cell suspension having an $OD_{630}$ of from 5 to 25. After incubation at 30° C. for a period of from 4 to 20 minutes, the microbial cells were removed by centrifugation. The amount of mandelic acid produced or a derivative thereof in the supernatant was determined in the same manner as in Example 1.

For comparison, the same procedures were followed, except for no sodium sulfite was used.

The results obtained are shown in Table 3.

TABLE 3

| Microorganism | Na₂SO₃ | Amount of Mandelic Acid Produced or Derivative Thereof R in Formula (III) (X: —COOH) | | | | | | | | |
|---|---|---|---|---|---|---|---|---|---|---|
| | | Phenyl | 2-Chloro-phenyl | 3-Chloro-phenyl | 4-Bromo-phenyl | 4-Nitro-phenyl | 4-Hydroxy-phenyl | 4-Amino-phenyl | 4-ethyl-phenyl | 4-Methoxy-phenyl |
| Alcaligenes sp. BC35-2 | present | 9.1 | 10.2 | 3.8 | 9.6 | 2.0 | 4.8 | 4.0 | 5.3 | 4.4 |
| | absent | 4.0 | 3.2 | 1.5 | 4.2 | 0.7 | 2.3 | 2.2 | 2.7 | 2.5 |
| Pseudomonas sp. BC13-2 | present | 6.3 | 8.8 | 7.1 | 0 | 5.6 | 8.4 | 5.3 | 4.2 | 0.8 |
| | absent | 3.8 | 3.0 | 2.9 | 0 | 2.6 | 4.0 | 2.1 | 2.6 | 0.2 |
| Caseobacter sp. BC-4 | present | 4.2 | 5.8 | 5.0 | 1.8 | 4.0 | 4.3 | 2.5 | 4.4 | 4.8 |
| | absent | 2.1 | 2.6 | 2.8 | 0.8 | 2.5 | 2.0 | 1.5 | 2.6 | 3.1 |
| Acinetobacter sp. BC9-2 | present | 2.7 | 0 | 1.2 | 2.5 | 1.8 | 3.4 | 2.6 | 1.7 | 1.4 |
| | absent | 1.3 | 0 | 0.5 | 1.2 | 1.1 | 1.8 | 1.2 | 0.8 | 0.7 |
| Nocardia asteroides IFO 3384 | present | 5.0 | 5.5 | 4.1 | 1.1 | 4.8 | 4.5 | 4.8 | 4.8 | 2.4 |
| | absent | 2.3 | 2.8 | 1.7 | 0.5 | 2.2 | 1.8 | 2.0 | 2.5 | 1.5 |
| Bacillus subtilis ATCC 21697 | present | 6.8 | — | — | — | — | — | — | — | — |
| | absent | 3.2 | — | — | — | — | — | — | — | — |
| Brevibacterium acetylicum IAM 1790 | present | 7.5 | 7.2 | 6.5 | 2.4 | 7.0 | 6.2 | 5.8 | 5.6 | 5.2 |
| | absent | 4.8 | 4.0 | 3.2 | 1.5 | 3.8 | 3.5 | 3.0 | 2.2 | 2.6 |
| Aureobacterium testaceum IAM 1561 | present | 13.0 | 12.4 | 10.2 | 9.7 | 9.0 | 10.7 | 10.7 | 11.1 | 10.0 |
| | absent | 6.2 | 6.5 | 5.5 | 5.1 | 5.2 | 6.3 | 5.7 | 6.0 | 4.9 |
| Alcaligenes fecalis ATCC 8750 | present | 1.2 | — | — | — | — | — | — | — | — |
| | absent | 0.5 | — | — | — | — | — | — | — | — |

EXAMPLE 4

Alcaligenes sp. BC35-2 (FERM No. 11265; FERM BP-3318) was suspended in 200 ml of a 50 mM phosphoric acid buffer at a concentration of $OD_{630}=25$. The cell suspension was divided into two halves, and 100 mM sodium sulfite was added to one half. To each half was added 0.48 g of mandelonitrile at 15° C. while stirring. After confirming that mandelonitrile was consumed and converted to mandelic acid, 0.48 g of mandelic acid was added in the same manner. The operation of the reaction and mandelonitrile replenishment was repeated until the hydrolysis reaction ceased. Table 4 below shows the amount of the finally produced mandelic acid.

TABLE 4

| Na₂SO₃ | Mandelic Acid Produced (g/l) |
|---|---|
| present | 166 |
| absent | 39 |

EXAMPLE 5

Microbial cells of Rhodococcus sp. HT40-6 (FERM No. 11774; FERM P-11774) were suspended in 1.5 ml of a 20 mM phosphoric acid buffer (pH=7.5) containing 14 mM mandelonitrile in the presence or absence of 100 mM sodium sulfite or sodium disulfite to a concentration of $OD_{630}=15$ and the suspension was shaken at 30° C. for 6 hours. After completion of the reaction, the microbial cells were removed by centrifugation and the amount of mandelamide in the supernatant was determined by liquid chromatography (column: SHODEX ODS F511A; carrier: 0.2M H₃PO₄/acetonitrile=4:1; monitor: 208 nm). Further, the optical purity of mandelamide was determined by using a column for optical resolution (CHIRALCEL CA-1 produced by Daicel Chemical Industries, Ltd., Japan; carrier: 100% ethanol). The results obtained are shown in Table 5 below.

TABLE 5

| SO₃⁻⁻Ion | Mandelamide Produced (mM) | Optical Purity of S-(+)-Mandelamide (%age) |
|---|---|---|
| absent | 5.5 | 99 |
| 100 mM Na₂SO₃ | 10.1 | 98 |
| 100 mM NaHSO₃ | 11.2 | 98 |

EXAMPLE 6

Brevibacterium acetylicum IAM 1790 was precultivated at 30° C. for 24 hours in a test tube (diameter: mm) containing 10 ml of a medium comprising 10 g/l of glucose, 5 g/l of polypeptone, 5 g/l of yeast extract and 3 g/l of malt extract (pH=7). The seed culture was inoculated into 100 ml of a medium having the following composition in a 500 ml-volume Erlenmeyer flask to a final concentration of 1% and cultured at 30° C. for 72 hours. The culture was centrifuged and the microbial cells collected were washed twice with a 5 mM phosphoric acid buffer (pH=7) to obtain 0.3 g of the microbial cells per culture.

| Medium Composition: | |
|---|---|
| Glycerol | 20 g |
| Yeast extract | 3 g |
| Dichloropantoylonitrile | 0.3 g |
| K₂HPO₄ | 3 g |
| MgCl₂ | 0.2 g |
| CaCl₂ | 40 mg |
| MnSO₄.4H₂O | 4 mg |
| FeCl₃.7H₂O | 0.7 mg |
| ZnSO₄.7H₂O | 0.1 mg |
| Distilled water | 1000 ml |
| pH = 7.2 | |

To 10 ml of a 50 mM phosphoric acid buffer (pH=7) containing 10 mM of pantoylonitrile as a substrate and a prescribed amount of sodium sulfite, sodium disulfite or sodium dithionite was added 0.15 mg/ml of the above-prepared microbial cells and the system was allowed to react at 30° C. for 15 minutes. After completion of the reaction, the reaction system was centrifuged to remove the microbial cells and the supernatant liquor was analyzed by high performance liquid chromatography using a SHODEX ODS F511A column. The results obtained are shown in Table 6 below.

TABLE 6

| Additive | | | |
|---|---|---|---|
| Kind | Concentration (mM) | Activity (U/mg) | Specific Activity (%) |
| None | — | 0.44 | 100 |
| Sodium sulfite | 5 | 0.75 | 172 |
|  | 10 | 1.06 | 242 |
| Sodium hydrogensulfite | 2 | 0.68 | 155 |
|  | 5 | 0.91 | 206 |
|  | 10 | 1.21 | 275 |
|  | 20 | 1.31 | 298 |
|  | 50 | 1.59 | 362 |
|  | 100 | 2.00 | 454 |
| Sodium dithionite | 2 | 0.82 | 187 |
|  | 5 | 0.95 | 216 |
|  | 10 | 1.32 | 300 |

EXAMPLE 7

Pseudomonas sp. BC12-2 (FERM P-11263) was cultured under the same manner as in Example 6, except the medium contained 0.3 g/l benzonitrile as an inducer instead of adding dichloropantoylonitrile. Cells were harvested and washed as described in Example 6. To the 20 ml of cell suspension (OD$_{630}$=30) in a 50 mM phosphoric acid buffer (pH 7.0), hydrogen cyanide (15 mM), benzaldehyde (15 mM), and sodium bisulfite (100 mM) were added, and the mixture was allowed to react at 30° C. for 6 hours. After the reaction, the microbial cells were removed and the supernatant analyzed as in Example 1.

As a result, it was found that 13 mM mandelic acid was produced and the optical purity of the product was 98 % age.

While the invention has been described in detail and with reference to specific examples thereof, it will be apparent to one skilled in the art that various changes and modifications can be made therein without departing from the spirit and scope thereof.

What is claimed is:

1. A process for biologically producing an α-hydroxyamide or an α-hydroxy acid represented by formula (III):

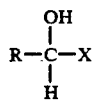

(III)

wherein R represents a substituted or unsubstituted alkyl group, a substituted or unsubstituted alkenyl group or a substituted or unsubstituted aryl group; and X represents an amido group or a carboxyl group, comprising reacting (a) an α-hydroxynitrile represented by formula (I):

wherein R is as defined above, or (b) a mixture of an aldehyde represented by formula (II):

wherein R is as defined above, and hydrogen cyanide, with a microorganism which produces such an amide or acid from the corresponding α-hydroxynitrile, wherein the reaction with a microorganism occurs in the presence of a sulfite ion, a disulfite ion or a dithionite ion.

2. The process of claim 1, wherein said α-hydroxyamide or α-hydroxy acid is an optically active compound.

3. The process of claim 1, wherein an α-hydroxy acid is produced.

4. The process of claim 3, wherein said microorganism is of a genus selected from the group consisting of Pseudomonas, Alcaligenes, Acinetobacter, Caseobacter, Corynebacterium, Brevibacterium, Nocardia, Rhodococcus, Arthrobacter, Bacillus, Aureobacterium, Enterobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium and Rhodopseudomonas.

5. The process of claim 4, wherein said microorganism is selected from the group consisting of Pseudomonas sp. BC13-2 (FERM BP-3319), Pseudomonas sp. BC15-2 (FERM BP-3320), Pseudomonas sp. SK13 (FERM BP-3325), Pseudomonas sp. SK31 (FERM P-11310), Pseudomonas sp. SK87 (FERM P-11311), *Pseudomonas synxantha* IAM 12356, Alcaligenes sp. BC12-2 (FERM P-11263), Alcaligenes sp. BC20 (FERM P-11264), Alcaligenes sp. BC35-2 (FERM BP-3318), Acinetobacter sp. BC9-2 (FERM BP-3317), Caseobacter sp. BC4 (FERM BP-3316), Caseobacter BC23 (FERM P-11261), *Corynebacterium nitrilophilus* ATCC 21419, *Brevibacterium acetylicum* IAM 1790, *Brevibacterium helvolum* ATCC 11822, Nocardia sp. N-775 (FERM BP-961), *Nocardia asteroides* IFO 3384, *Nocardia calcarea* KCC A0191, *Nocardia polychromogenes* IFM 19, Rhodococcus sp. SK70 (FERM P-11304), Rhodococcus sp. SK92 (FERM BP-3324), Rhodococcus sp. HR11 (FERM P-11306), *Rhodococcus rhodochrous* ATCC 12674, *Rhodococcus rhodochrous* ATCC 19140, *Rhodococcus rhodochrous* ATCC 33258, *Rhodococcus erythropolis* IFM 155, *Rhodococcus erythropolis* IFO 12320, *Rhodococcus erythropolis* IFO 12538, *Rhodococcus erythropolis* IFO 12540, Arthrobacter sp. SK103 (FERM P-11300), Arthrobacter sp. HR1 (FERM BP-3323), Arthrobacter sp. HR4 (FERM P-11302), *Arthrobacter oxydans* IFO 12138, *Bacillus subtilis* ATCC 21697, *Bacillus licheniformis* IFO 12197, *Bacillus megaterium* ATCC 25833, *Aureobacterium testaceum* IAM 1561, Enterobacter sp. SK12 (FERM BP-3322), *Escherichia coli* IFO 3301, *Micrococcus luteus* ATCC 383, *Micrococcus varians* IAM 1099, *Micrococcus roseus* IFO 3768, *Streptomyces griseus* IFO 3355, Flavobacterium sp. SK150 (FERM P-11645), *Flavobacterium falvescens* ATCC 8315, *Aeromonas punctata* IFO 13288,

*Mycoplana dimorpha* ATCC 4297, *Cellulomonas fimi* IAM 12107, *Erwinia herbicola* IOF 12686 and *Candida quilliermondii* IFO 0566.

6. The process of claim 1, wherein an α-hydroxyamide is produced.

7. The process of claim 6, wherein said microorganism is of a genus selected from the group consisting of Rhodococcus, Corynebacterium, Pseudomonas, Arthrobacter, Alcaligenes, Bacillus, Bacteridium, Micrococcus, Brevibacterium and Nocardia.

8. The process of claim 7, wherein said microorganism is selected from the group consisting of *Rhodoccus rhodochrous* ATCC 33278, *Rhodococcus erythropolis* IFO 12320, *Corynebacterium nitrilophilus* ATCC 21419, Pseudomonas sp. SK 87 (FERM P-11311), Arthrobacter sp. HR1 (FERM BP-3323) and Alcaligenes sp. BC16-2 (FERM BP-3321).

9. The process of claim 1, wherein said α-hydroxynitrile comprises lactonitrile, α-hydroxy-n-butyronitrile, α-hydroxy-n-hexylonitrile, α-hydroxy-n-heptylonitrile, α-hydroxy-n-octylonitrile, α,γ-dihydroxy-β,β-dimethylbutyronitrile, acrolein cyanhydrin, methacrylaldehyde cyanhydrin, 3-chlorolactonitrile, 4-methylthio-α-hydroxybutyronitrile, mandelonitrile or 2-naphthyaldehyde cyanhydrin.

* * * * *